(12) United States Patent
Shubin, Sr. et al.

(10) Patent No.: US 9,039,600 B2
(45) Date of Patent: May 26, 2015

(54) SYSTEMS AND METHODS RELATED TO COLLECTION OF BIOLOGICAL FLUIDS

(71) Applicant: Steven A. Shubin, Sr., Dripping Springs, TX (US)

(72) Inventors: Steven A. Shubin, Sr., Dripping Springs, TX (US); Steven A. Shubin, Jr., Santa Fe, NM (US)

(73) Assignee: Steven A. Shubin, Sr., Dripping Springs, TX (US)

( * ) Notice: Subject to any disclaimer, the term of this patent is extended or adjusted under 35 U.S.C. 154(b) by 317 days.

(21) Appl. No.: 13/796,223

(22) Filed: Mar. 12, 2013

(65) Prior Publication Data
US 2014/0275758 A1    Sep. 18, 2014

(51) Int. Cl.
| | | |
|---|---|---|
| *A61F 5/00* | (2006.01) | |
| *B29C 45/26* | (2006.01) | |
| *A61B 10/00* | (2006.01) | |
| *A61F 5/453* | (2006.01) | |
| *A61H 19/00* | (2006.01) | |

(52) U.S. Cl.
CPC ......... *B29C 45/2602* (2013.01); *A61B 10/0058* (2013.01); *A61F 5/453* (2013.01); *A61H 19/32* (2013.01); *A61H 2201/1253* (2013.01)

(58) Field of Classification Search
CPC ..... A61B 10/0058; A61F 5/453; A61H 19/32
USPC ....................... 600/38–41, 573–580; 604/317, 604/322–324, 347–349
See application file for complete search history.

(56) References Cited

U.S. PATENT DOCUMENTS

| | | |
|---|---|---|
| 5,370,131 A | 12/1994 | Hess |
| 5,466,235 A | 11/1995 | Shubin |
| 5,782,818 A | 7/1998 | Shubin |
| 5,806,523 A | 9/1998 | Shubin, Sr. |
| 5,807,360 A | 9/1998 | Shubin, Sr. |
| 2010/0041944 A1 | 2/2010 | Levy |

FOREIGN PATENT DOCUMENTS

| | | |
|---|---|---|
| EP | 1716813 A1 | 11/2006 |
| WO | 2011145580 A1 | 11/2011 |

*Primary Examiner* — John Lacyk
(74) *Attorney, Agent, or Firm* — Conley Rose, P.C.

(57) ABSTRACT

Collection of biological fluids. At least some of the example embodiments are polymeric sleeves including: an elongate body that defines a first end, a second end opposite the first end, and a longitudinal central axis; a main passageway through the elongate body parallel to the central axis, the main passageway extends from the first end to the second end, and the main passageway defines a first aperture on the first end and a second aperture on the second end; a first member suspended over the first aperture on the first end, the first member defines a first initial passageway parallel to the main passageway, and the first member and first end define an interior volume; and a first vent opening defined in part by the first member, the first vent opening distinct from the passageways, and the first vent opening fluidly couples the interior volume to atmosphere pressure.

15 Claims, 13 Drawing Sheets

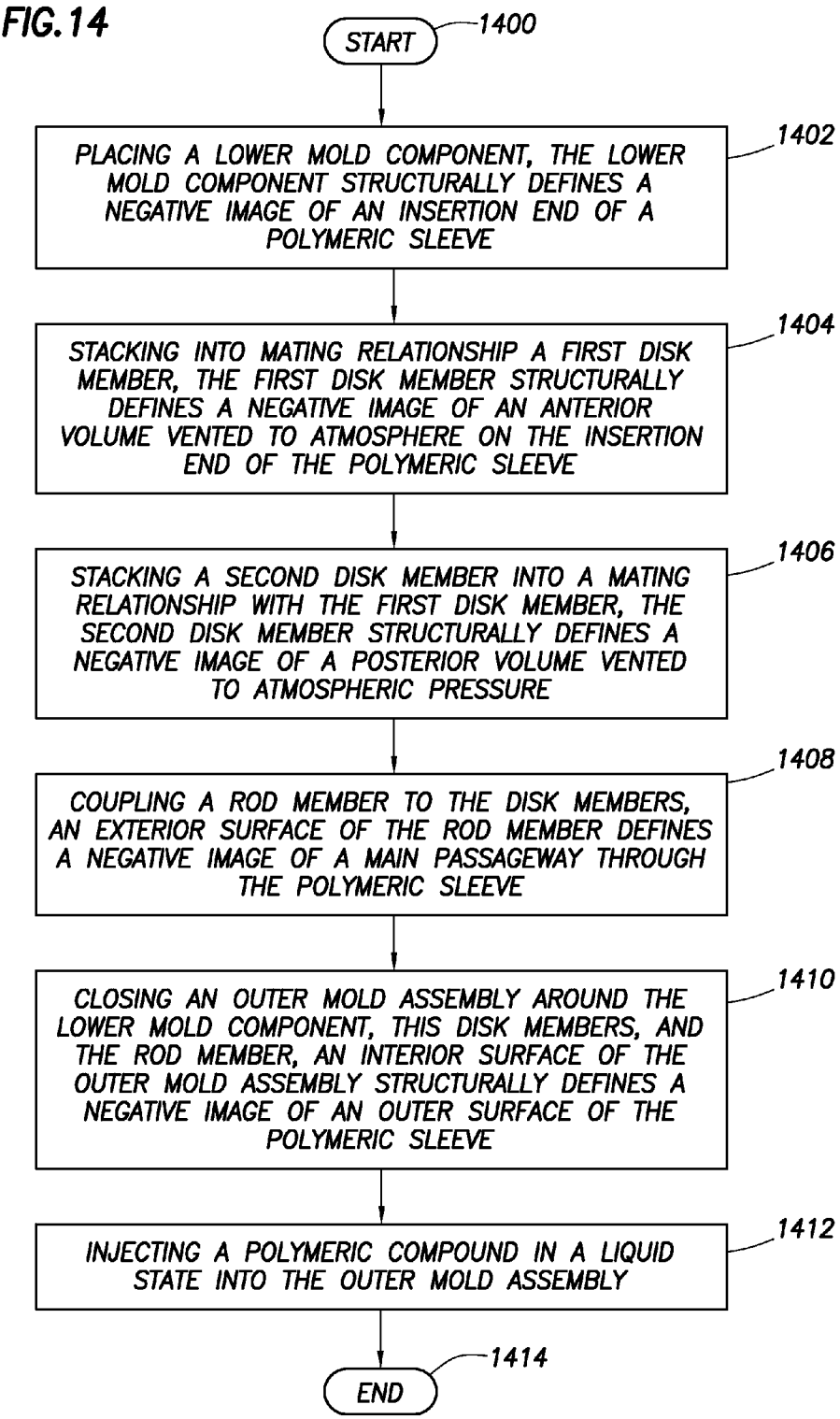

SYSTEMS AND METHODS RELATED TO COLLECTION OF BIOLOGICAL FLUIDS

BACKGROUND

In recent years there have many advancements in devices for stimulation and collection of biological fluids, particularly seminal fluids. For example, FLESHLIGHT® brand products are devices that aid in stimulation and collection of seminal fluids through ejaculation. Many such products visually mimic genitalia, and also attempt to simulate the feel of copulation.

Recent studies have found that prostate health in human males may be related to frequency of ejaculation. In particular, infrequent ejaculation can lead to swelling of the prostate, known as congestive prostatitis, and may also increase the cancer risk in human males. Some medical sources suggest an ejaculation frequency of three to four times per week ensures good prostate health and reduces cancer risk. One study found a 14% lower lifetime prostate cancer rate for men who ejaculate between 13 and 20 times per month, and an upwards of 33% lower lifetime prostate cancer risk for men who ejaculate 21 times or more each month. Devices for stimulation and collection of seminal fluids may aid in achieving higher ejaculations rates among men, particularly the unmarried and long-married.

Beyond the prostate health effects of ejaculation, devices for stimulation and collection of seminal fluids through ejaculation may also assist in reversing desensitization issues. That is, repeated masturbatory stimulation of the penis using the hand or rough cloth can lead to desensitization of the penis, particularly in the absence of lubrication. Desensitization can then result in erectile dysfunction during copulation. Use of properly lubricated devices designed specifically for the stimulation and collection of seminal fluid may help reverse the desensitization issues, and thus reduce the occurrence of erectile dysfunction related to desensitization issues.

Any improvement in devices for stimulation and collection of seminal fluid, in view of the positive health benefits, would be beneficial.

BRIEF DESCRIPTION OF THE DRAWINGS

For a detailed description of exemplary embodiments, reference will now be made to the accompanying drawings in which:

FIG. 14 shows a method in accordance with at least some embodiments.

NOTATION AND NOMENCLATURE

Figure 1:
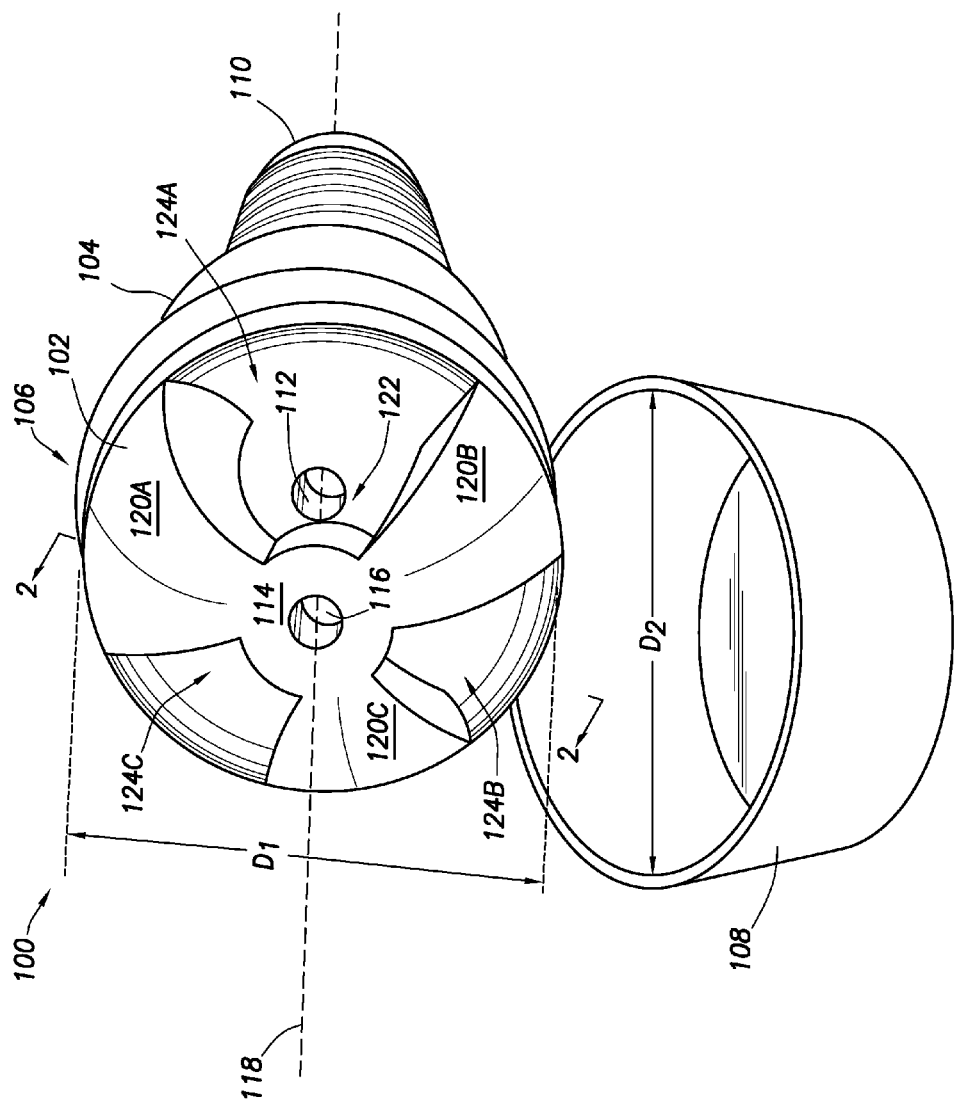
FIG. 1 shows a perspective view of system in accordance with at least some embodiments.

Certain terms are used throughout the following description and claims to refer to particular system components. As one skilled in the art will appreciate, different companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection.

"Bifurcate" shall mean that an area or volume is divided, but shall not speak to relative sizes of the divided areas or volumes.

"Removably coupled" shall mean that a first device couples to second device in such a way that the first device can be mechanically separated from the second device without the use of tools, without cutting either the first device or the second device, and without full or partial destruction of either the first device or the second device.

"Mold surface" shall mean any exposed surface area within the lower mold component (which lower mold component may be referred as a tool or tooling), whether or not the exposed surface directly abuts a disk member or defines a cavity or channel.

"Over," "above," and "below" are relative terms related to the various devices described herein. In relation to a seminal fluid collection device, the terms "over," "above," and "below" shall be in reference to a seminal fluid collection device with the insertion end held upwardly for viewing. In relation to a mold system, the terms "above" and "below" shall be in reference to mold components stacked in relation to gravity.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The various embodiments are directed to systems, and related methods, of stimulation of and collection of biological fluids, particularly seminal fluid. The various example systems were developed in the context of devices for use by human males, and thus the description that follows is based on the developmental context; however, the systems and methods may find other uses, such as veterinary uses (e.g., horses, dogs), and thus the developmental context shall not be viewed as a limitation as to the scope of the applicability of the devices.

FIG. 1 shows a perspective view of system 100 in accordance with at least some embodiments. In particular, the system 100 comprises a polymeric sleeve 102 at least partially disposed within an interior volume of an outer cover 104 of rigid material, such as plastic. In the view of FIG. 1, only the insertion end 106 of the polymeric sleeve 102 is visible, as the balance of the polymeric sleeve resides within the outer cover 104. The polymeric sleeve 102 may be made of a thermoplastic elastomer gel (TPE) of low durometer rating, or other material, such as silicon, polyvinyl chloride (PVC), or elastomeric rubber. The system 100 may further comprise a cover or lid 108 that defines an inside diameter D2 slightly larger than the outside diameter of the D1 of the insertion end 106 of the polymeric sleeve 102 such that, when not in use, the lid 108 may be telescoped over the insertion end 106 and couple to the outer cover 104. The lid 108 may, for example, protect the insertion end 106 from damage when not in use. The system 100 may further comprise a second cap or lid 110 that couples to the outer cover 104 opposite the lid 108. The lid 110 may act, in some cases and in conjunction with other features of the outer cover 104, as a controllable vent mechanism during use (discussed more below).

The insertion end 106 of the example system of FIG. 1 comprises a main aperture 112 which leads to a main passageway (the main passageway not visible in FIG. 1, but discussed more below). Suspended over the main aperture 112 is a first flange member 114 that defines an initial passageway 116. In the example system, the initial passageway 116 is coaxial with the main passageway, and both the initial passageway 116 and main passageway are coaxial with the longitudinal central axis 118 of the polymeric sleeve 102. In other systems, however, the initial passageway 116 may be offset from the main passageway, and one or both the initial passageway 116 and the main passageway may be offset (and/or non-parallel) to the longitudinal central axis 118 of the polymeric sleeve 102.

Still referring to FIG. 1, the flange member 114 is supported in the example system by three stanchion portions 120A, 120B, and 120C. As will be discussed more thoroughly below, the entire polymeric sleeve 102 (including the flange member and stanchion portions) may be created from a single molding of polymeric material, and thus while the flange member 114 and the stanchion portions 120 are separately named for ease of discussion, the separate naming convention shall not obviate that the separately named components are actually a single, continuous piece of polymeric material. The stanchion portions 120 extend from near an outer diameter of the insertion end 106 toward the longitudinal central axis 118 to suspend the flange member 114 over the main aperture 112. Though FIG. 1 shows an example system with three stanchion portions 120, in other cases as few as two stanchion portions 120 may be used (e.g., disposed on opposite sides of the flange portion 114), or greater than three stanchion portions may be used (e.g., four or more).

The flange member 114 and stanchion portions 120 protrude outwardly from the main aperture 112. Moreover, in some example systems, and as shown, the main aperture 112 is formed in a basin-like area such that there is an interior volume 122 defined between the flange member 114 and the polymeric material defining the main aperture 112. Rather than being a sealed interior volume, however, the interior volume 122 is vented to atmospheric pressure by way of openings defined between the stanchion portions 120. In particular, in the example system three vent openings 124A, 124B, 124C are defined by the stanchion portions 120. During certain portions of use of the system 100 the flange portion 114 may collapse toward the main aperture 112, and in some cases the bottom side of the flange member 114 may abut the polymeric material that forms the main aperture 112. At least some of the air displaced by the collapse of the flange member 114 toward the main aperture 112 may escape the interior volume 122 through the vent openings 124. Likewise, air that flows back in as the flange member 114 is pulled away from the main aperture 112 flows through the vent openings 124. By comparison, air displaced from the main passageway, such as by insertion of the penis into the main aperture 112, moves along the main passageway and vents at the outer cover 104 at or near the lid 110 on the vent end. Likewise, air that flows back in the main passageway, such as during withdrawal of the penis out of the main passageway, moves in through the outer cover 104 at or near the lid 110 and then along the main passageway.

Figure 2:
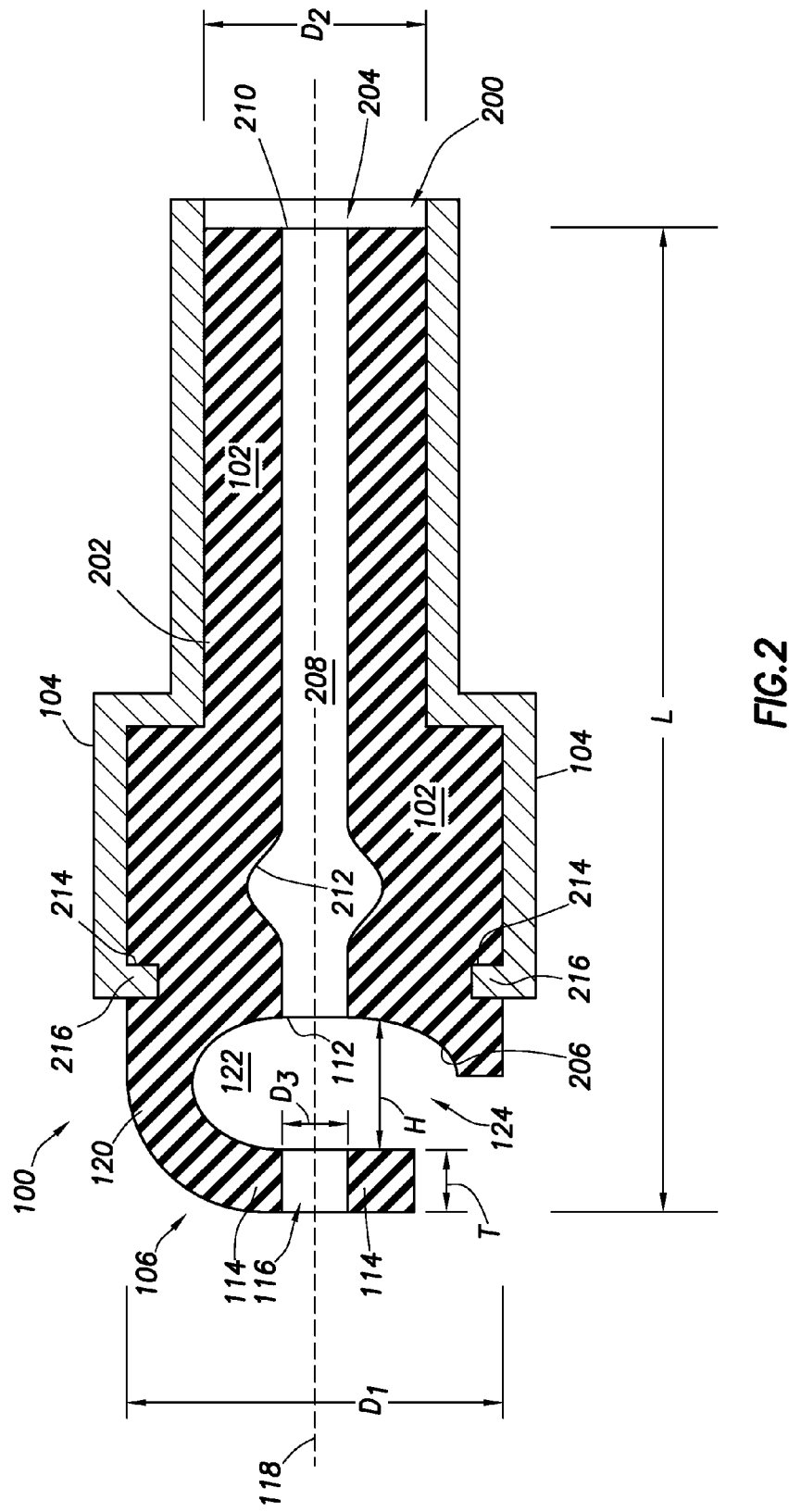
FIG. 2 shows a cross-sectional elevation view in accordance with at least some embodiments.

FIG. 2 shows a cross-sectional elevation view of the system 100 of FIG. 1, taken substantially along line 2-2 of FIG. 1. In particular, FIG. 2 shows a portion of the outer cover 104 and the polymeric sleeve 102. The outer cover 104 defines an internal volume 200 as well as the longitudinal central axis 118. The polymeric sleeve 102 is partially disposed within the internal volume 200, and in the example system shown, the insertion end 106 resides at least partially outside the internal volume 200 of the outer cover 104. The polymeric sleeve 102 defines an elongate body 202 and a vent end 204 opposite the insertion end 106. In some example systems, the overall length L is at least two times the diameter D1, but other proportions may be equivalently used. In the view of FIG. 2, the initial passageway 116 is shown, along with the flange member 114, and stanchion portion 120. Moreover, the basin-like structure 206 is visible, within which the main aperture 112 is formed, along with the interior volume 122 and vent opening 124.

FIG. 2 further shows, in cross-sectional view, the main passageway 208. The main passageway 208 spans from the main aperture 112 on the insertion end 106 to a vent aperture 210 on the vent end 204. In some example systems, the main passageway 208 defines a constant internal diameter from the main aperture 112 to the vent aperture 210; however, in other cases, and as shown, the main passageway 208 has one or more features thought to enhance the stimulation characteristics. In the example of FIG. 2, the main passageway 208 defines an increased internal diameter annular area 212. Other features are possible, including inward projecting features, such as "rifling", or various tabs or protrusions. Note, however, that the internal volume created by the annular area 212 vents along the main passageway 208. That is, during insertion of the penis, air displaced from the annular area 212 travels along the main passageway 208 and out the vent aperture 210. Likewise, during withdrawal of the penis, air drawn back in the annular area 212 will enter the vent aperture 210 and travel along the main passageway 208.

In some cases, the polymeric sleeve 102 may define an annular groove 214 on an outer diameter thereof. Likewise, the outer cover 104 may define a corresponding annular ring 216 such that, when the polymeric sleeve is telescoped within the internal volume 200, the annular ring 216 may couple within the annular groove 214. The ring/groove combination may help hold the polymeric sleeve 102 in place during use, and in particular the ring/groove combination may reduce reciprocatory movement of the polymeric sleeve during use of the device 100.

In one example system, such as shown in FIGS. 1 and 2, the diameter D1 may be about three inches, the diameter D2 may be about 2.25 inches, and the length L may be about nine inches. The thickness T of the flange member 114 may be about 0.5 inches, but a thicker flange member may be molded if the durometer rating of the cured polymeric material is lower. Likewise, a thinner flange member may be molded if the durometer rating of the cured polymeric material is higher. Inasmuch as the flange member 114 and stanchion portion 120 are a contiguous structure, the stanchion portion 120 may likewise have a thickness of about 0.5 inches at its thinnest portion. It follows from the example thickness of the flange member 114 that the length of the initial passageway 116 may be about 0.5 inches. The diameter D3 of the initial passageway 116 may be about 0.5 inches, and likewise the diameter of the main passageway 208 at the main aperture 112 may be about 0.5 inches. In other cases, however, the diameter of the initial passageway D3 may be larger or smaller than the diameter of the main passageway 208 at the main aperture 112. Finally, the height H that the flange member 114 is suspended over the main aperture 112 defined in the bottom of the basin-like structure 206 may be about one inch in some embodiments. As discussed immediately below, however, additional flange members may also be present.

Figure 3:
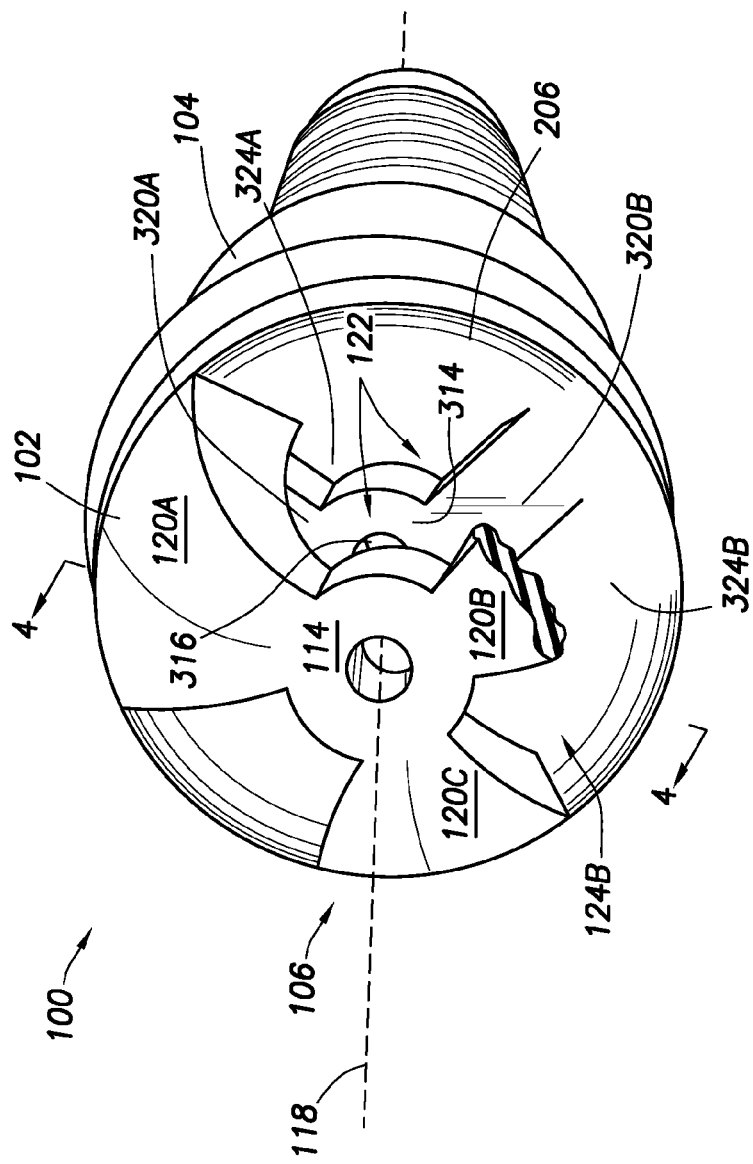
FIG. 3 shows a perspective, partial cut-away view, in accordance with at least some embodiments.

FIG. 3 shows a perspective, partial cut-away, view of a system 100 in accordance with other example embodiments. In particular, the system 100 comprises a polymeric sleeve 102 at least partially disposed within an interior volume of an outer cover 104 of rigid material, such as plastic. In the view of FIG. 3, only the insertion end 106 of the polymeric sleeve 102 is visible, as the balance of the polymeric sleeve resides within the outer cover 104. The system 100 may further comprise a cover or lid (not specifically shown) that telescopes over the insertion end 106 and couples to the outer cover 104. Likewise, the system 100 may further comprise a second cap or lid (again not specifically shown) that couples to the outer cover 104 opposite the insertion end 106.

The insertion end 106 in the example system of FIG. 3 comprises a main aperture which leads to a main passageway, but neither the main aperture nor the main passageway are visible in FIG. 3. Suspended over the main aperture is a first flange member 114 that defines an initial passageway 116, and also suspended over the main aperture is a second flange member 314 that defines a second initial passageway 316. In the example system, the passageway 116 is coaxial with the passageway 316, and the passageway 316 is coaxial with the main passageway. Moreover, in the example system, the passageway 116, passageway 316, and main passageway are coaxial with the longitudinal central axis 118 of the polymeric sleeve 102. In other systems, however, the passageways 116 and 118 may be offset from each other, as well as offset from the main passageway.

Still referring to FIG. 3, the flange member 114 is supported in the example system by three stanchion portions 120A, 120B, and 120C, but in the view of FIG. 3 the stanchion portion 120B has been removed to provide better visibility to the flange member 314 below. The flange member 314 is supported in the example system by three stanchion portions 320, though only stanchion portions 320A and 320B are visible in FIG. 3. As with the flange member 114 and stanchion portions 120, the entire polymeric sleeve 102 (including the flange members and stanchion portions) may be created from a single molding of polymeric material, and thus while the flange member 314 and the stanchion portions 320 are separately named for ease of discussion, the separate naming convention shall not obviate that the separately named components are actually a single, continuous piece of polymeric material. The stanchion portions 320 extend from the basin-like-structure 206 (near an outer diameter of the insertion end 106) toward the longitudinal central axis 118 to suspend the flange member 314 over the main aperture. In the example system of FIG. 3, the stanchion portions 320 are radially aligned with the stanchion portions 120; however, radial alignment is not required, and in other cases the radial direction in which the stanchion portions 320 extend may be different, and in some cases non-overlapping with the radial direction in which the stanchion portions 120 extend.

As with the flange member 114, the flange portion 314 may both collapse or translate toward the main aperture during certain portions of use, and may also be stretched away from the main aperture during other portions of use. Though three stanchion portions 320 are discussed in reference to FIG. 3, in other cases as few as two stanchion portions 320 may be used (e.g., disposed on opposite sides of the flange portion 314), or greater than three stanchion portions may be used (e.g., four or more). Moreover, the number of stanchion portions 320 need not be the same as the number of stanchion portions 120. For example, operable systems may comprise three stanchion portions 120 and two stanchion portions 320, or vice-versa.

The flange member 314 and stanchion portions 320 may protrude outward from the main aperture 112, or as shown the upper surfaces of the flange member 314 and stanchion portions 320 may define and reside within a plane. Moreover, the interior volume 122 defined between the flange member 114 and the basin-like structure 206 may be bifurcated by the flange member 314 and stanchion portions 320. The portion of the interior volume 122 defined between the basin-like structure 206 and the flange member 314 may be vented to atmospheric pressure by way of three vent openings 324 (only vent openings 324A and 324B are visible in FIG. 3), which vent openings are defined by the stanchion portions 320. During certain portions of use of the system 100, the flange member 314 may collapse toward the main aperture, and in some cases the bottom side of the flange member 314 may abut the basin-like structure 206. At least some of the air displaced by the collapse of the flange member 314 toward the main aperture may escape the interior volume 122 through the vent openings 324 (and 124). Likewise, air that flows back in as the flange member 314 is pulled away from the main aperture flows through the vent openings 324 (and 124).

Figure 4:
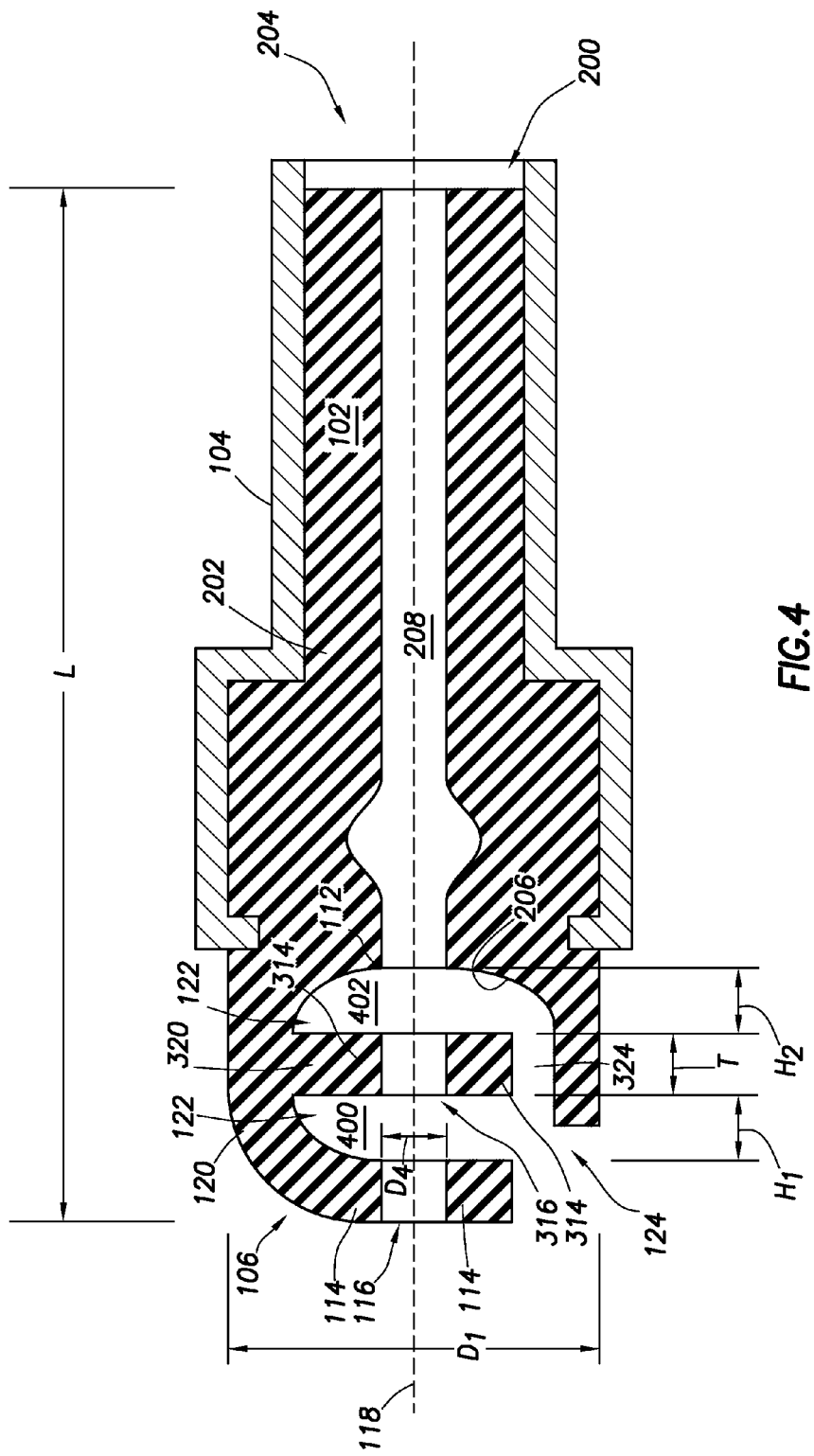
FIG. 4 shows a cross-sectional elevation view in accordance with at least some embodiments.

FIG. 4 shows a cross-sectional elevation view of the system 100 of FIG. 3, taken substantially along line 4-4 of FIG. 3. In particular, FIG. 4 shows a portion of the outer cover 104 and the polymeric sleeve 102. As before, the outer cover 104 defines an internal volume 200 as well as the longitudinal central axis 118. The polymeric sleeve 102 is partially disposed within the internal volume 200, and in the example system shown the insertion end 106 resides at least partially outside the internal volume 200 of the outer cover 104. The polymeric sleeve 102 defines an elongate body 202 and a vent end 204 opposite the insertion end 106. In some example systems, the overall length L is at least two times the diameter D1, but other proportions may be equivalently used. In the view of FIG. 4, the initial passageway 116 is shown, along with the flange member 114, and stanchion portion 120. Moreover, the basin-like structure 206 is visible, within which the main aperture 112 is formed, along with the interior volume 122 and vent opening 124.

FIG. 4 further shows the passageway 316, along with the flange member 314, and stanchion portion 320. The flange member 314 is disposed between the first flange member 114 and the main aperture 112 within the interior volume 122. Moreover, the flange member 314 and stanchion portions 320 bifurcate the interior volume 122 into an anterior volume 400 (between the flange member 114 and the flange member 314) and a posterior volume 402 (between the flange member 314 and the main aperture 112). Also visible in FIG. 4 is the vent opening 324. The remaining portions of the polymeric sleeve (e.g., the main passageway 208) may be the same as discussed with respect to FIG. 2, and thus the discussion will not be repeated here.

In the example system of FIG. 4, the vent openings 124 vent the anterior volume 400 to atmospheric pressure. The vent openings 324 likewise vent the posterior volume 402 to atmospheric pressure. In the case of FIG. 4, the posterior volume 402 vents through the anterior volume 400, but in other cases a separate flow path to a point outside the polymeric sleeve 102 could be used.

In one example system, such as shown in FIGS. 3 and 4, the various diameters, thicknesses and lengths discussed with respect to FIG. 2 likewise apply. The thickness T of the flange member 314 may be about 0.5 inches, but a thicker flange member may be molded if the durometer rating of the cured polymeric material is lower. Likewise, a thinner flange member may be molded if the durometer rating of the cured polymeric material is higher. Inasmuch as the flange member 314 and stanchion portion 320 are a contiguous structure, the stanchion portion 320 may likewise have a thickness of about 0.5 inches at its thinnest portion. While the flange member 114 and flange member 314 are discussed to have the same thicknesses, in other cases the thicknesses may vary as between the flange members. It follows from the example thickness of the flange member 314 that the length of the second initial passageway 316 may be about 0.5 inch. The diameter D4 of the passageway 316 may be about 0.5 inch, but in other cases the diameter of the passageways may be larger or smaller than each other, and larger or smaller than the diameter of the main passageway 208 at the main aperture 112. The height H1 that the flange member 114 is suspended over the flange member 314 (measured from the underside of the flange member 114 to the top side of the flange member 314) may be about 0.5 inch in some embodiments. Moreover, the height H2 that the flange member 314 is suspended over bottom portion of the basin-like structure 206 (measured from the underside of the flange member 314 to the top side of the basin-like structure at or near the main aperture 112) may be about 0.5 inch in some embodiments.

Figure 5:
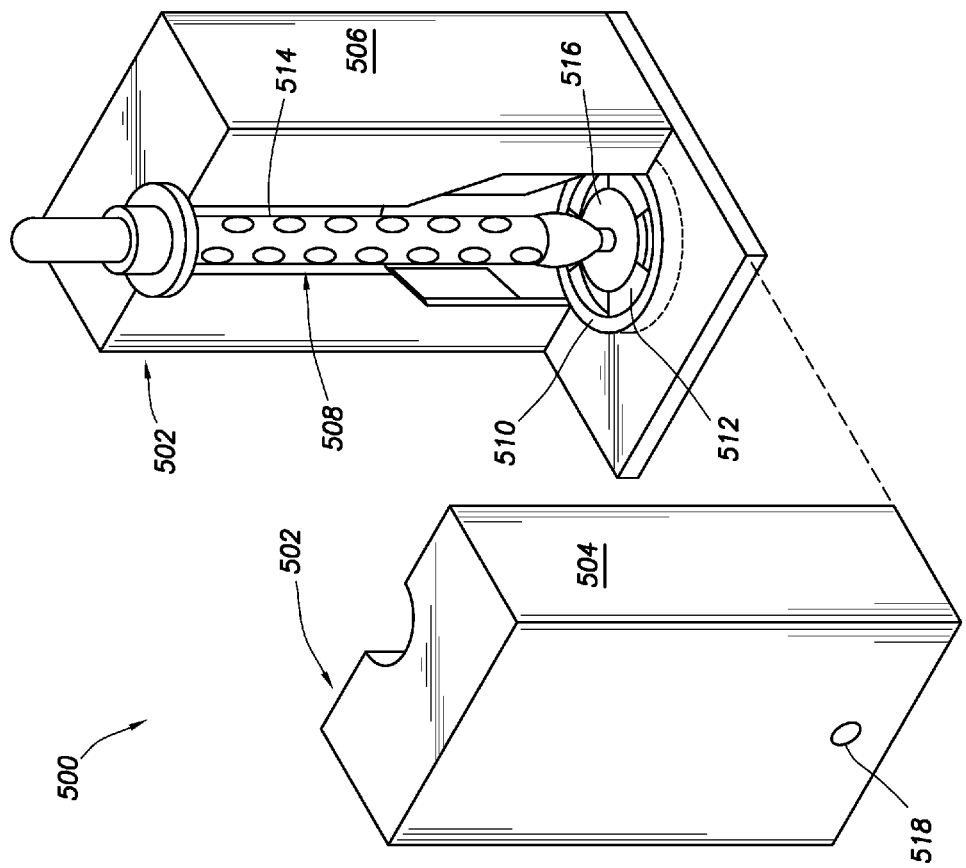
FIG. 5 shows a perspective view of a mold assembly in accordance with at least some embodiments.

The specification now turns to example methods of creating the polymeric sleeves. FIG. 5 shows a perspective view of a mold system 500 in accordance with at least some embodiments. In particular, FIG. 5 shows an outer mold assembly 502 comprising first mold member 504 and second mold member 506. Each mold member 504 and 506 defines an interior surface, but in the view of FIG. 5 only the interior surface 508 of mold member 506 is visible. The interior surface 508 of mold member 506 forms half a negative image of the exterior surface of the polymeric sleeve 102 spanning from the annular groove 214 to the vent end 204. Likewise, the interior surface of the mold member 504 forms the other half of the negative image of the exterior surface of the polymeric sleeve 102 from the annular groove 214 to the vent end 204.

The mold system 500 further comprises a lower mold component 510 placed in operational relationship to the interior surfaces defined by the outer mold assembly 502. The lower mold component structurally defines a negative image of the outer portions of the insertion end 106 of the polymeric sleeve 102. An example lower mold component 510 is discussed in greater detail with respect to FIG. 6. Suffice it to say, for now, that the lower mold component 510 defines a negative image of at least a portion of the flange member 114 and stanchions 120. In some example systems, the various mold components, lower mold component, and disk members (discussed more below) may be milled from metallic material, such as aluminum. However, other materials (e.g., high density plastics) may also be used. Stacked on the lower mold component 510 is a disk member 512. In systems having only a single interior volume 122, the disk member 512 defines a negative image of the interior volume (e.g., FIGS. 1 and 2). Stated otherwise, during the injection molding process the disk member 512 resides within a volume such that no polymeric material may fill and/or occupy the volume, and thus the single interior volume is created based on presence of the disk member 512 during the injection and curing process. In systems having only a single interior volume, the disk member 512 couples to a rod member 514. An exterior surface of the rod member 514 defines the negative image of the interior surface of the main passageway through the polymeric sleeve.

In systems defining both an anterior volume and a posterior volume (e.g., FIGS. 3 and 4), stacked on the disk member 512 is another disk member 516. The disk member 516 defines a negative image of the posterior volume. Stated otherwise, during the injecting molding process the disk member 516 resides within a volume such that no polymeric material may fill and/or occupy the volume, thus creating the posterior volume based on presence of the disk member 516 during the injection and curing process. In systems having both the anterior and posterior volumes, the rod member 514 couples to the disk member 516, with the rod member 514 again creating the main passageway in the injection molding process.

The molding process may involve stacking the various disks in the lower mold component, and coupling the rod member 514 to the upper-most disk member 512 or 516. The outer mold assembly 502 is closed around the various components and held in place in some fashion. The polymeric material in liquid form is injected through an injection port into the volume defined by the interior surface 508, such as injection through injection aperture 518. The polymeric material in liquid form fills the volume defined by the interior surface 508, displacing the air, and then the polymeric material is allowed to cure. Once cured, the outer mold assembly 502 is again opened, the rod member 514 withdrawn from the main passageway, the disk member 512 is removed from its respective volume (e.g., interior volume 122, or anterior volume 400), and if used the disk member 516 removed from the posterior volume 402. Either before or after removing the rod member and disk member(s), the polymeric sleeve 102 may be removed from the lower mold component 510. Trimming of the polymeric sleeve 102 may be performed, such as to remove the polymeric material that cured inside the injection aperture, and any mold seams or marks formed by the interface of the outer mold assembly. In some cases, the polymeric sleeve 102 created may be treated with compound to reduce surface tension (such as by application of talcum powder). The specification now turns to a more detailed description of example lower mold component and example disk members.

Figure 6:
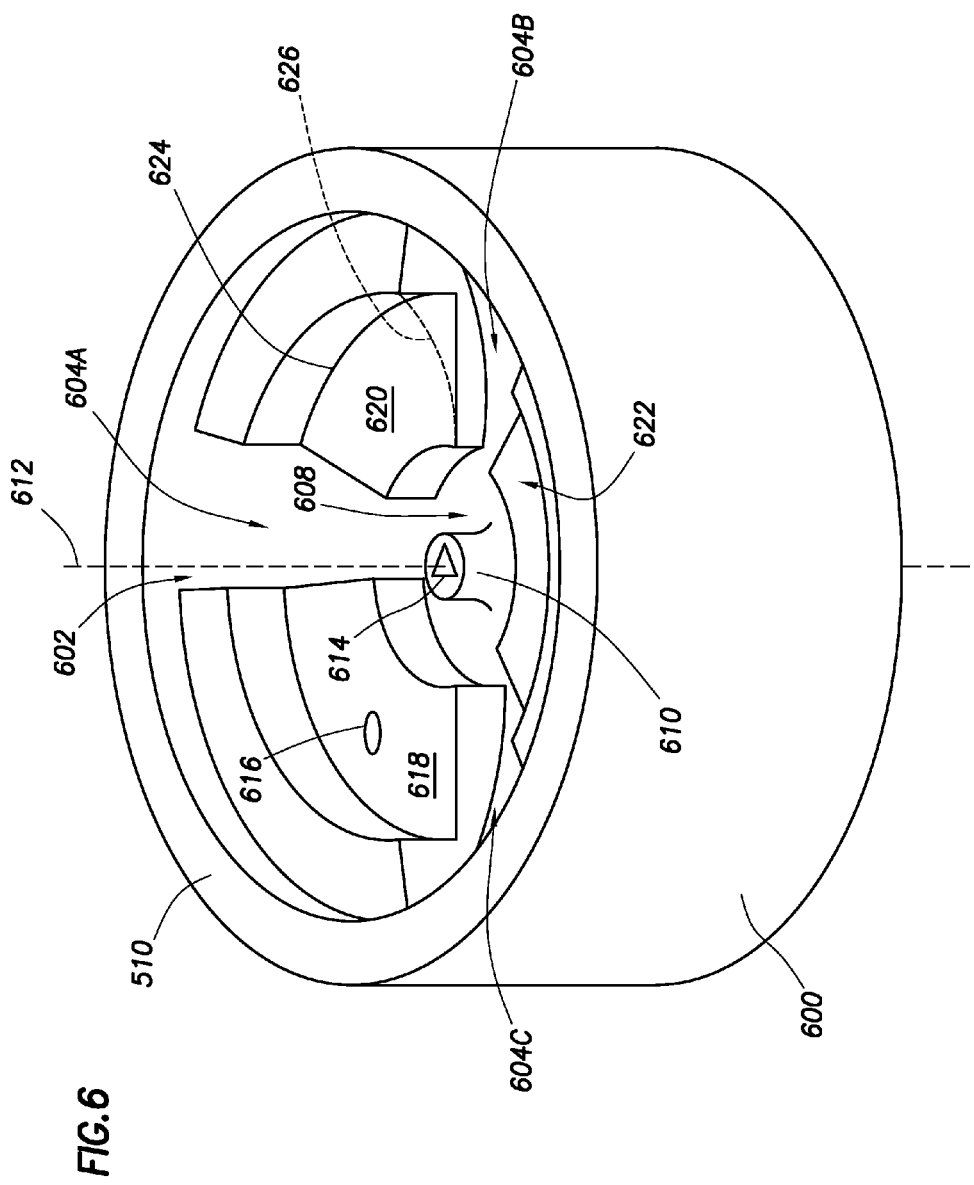
FIG. 6 shows a perspective view of lower mold component in accordance with at least some embodiments.

FIG. 6 shows a perspective view of a lower mold component in accordance with an example system, where the lower mold component may be used to create an insertion end 106 of a polymeric sleeve similar to those shown in FIGS. 1 and 3. In particular, the lower mold component 510 defines an exterior surface 600 and a mold surface 602 defined on an interior surface of the lower mold component 510. In the example lower mold component 510 of FIG. 6, the mold surface 602 defines three channels 604A, 604B, and 604C. The channels 604 extend from the largest inside diameter of the lower mold component 510 to a central area 608. Defined within the central area 608 is a protrusion or butte 610, which butte 610 may be centered within the mold surface 602 along the longitudinal central axis 612.

The mold surface 602 of the lower mold component 510 defines a negative image of the outer-most portions of the insertion-end 106 of the polymeric sleeve 102. For example, the channels 604 are the negative image of the stanchion portions 120. The central area 608 is the negative image of the flange member 114. The butte 610 is the negative image of at least a portion of the initial passageway 116. Stated otherwise, during the injection molding process the polymeric material, in liquid form, is forced into the channels 604 and central area 608. After curing of the polymeric material, the polymeric sleeve may be removed from the lower mold assembly 510, and thus the outer surface of the insertion end 106 of the polymeric sleeve 102 is formed.

Still referring to FIG. 6, a few additional features are discussed as a precursor to discussion of the first disk member. In particular, in some cases a particular rotational alignment of the first disk member with the lower mold component 510 is used, and thus the lower mold component 510 may have one or more features that assist in the alignment process. For example, the lower mold component 510 of FIG. 6 has an alignment feature 614 defined in butte 610. The example alignment feature 614 is an aperture defining a triangular cross-section, though other cross-sectional shapes may be used (e.g., square, rectangle, hexagon). A corresponding feature of the first disk member (discussed more below) has a shape that telescopes into the example alignment feature, thus ensuring proper rotational alignment. In other example cases, the lower mold component 510 may define a dimple feature 616 at any convenient location, and as shown in shoulder region 618. The dimple feature as shown is a concave dimple or divot into the material of the lower mold component 510, but convex features are likewise contemplated. The first disk member may have a corresponding feature (e.g., a convex feature if dimple feature 616 is concave, or a concave feature if dimple feature 616 is convex).

Finally, the example lower mold component 510 of FIG. 6 defines a series of shoulder regions. Shoulder region 618 was discussed with respect to dimple feature 616, but additional shoulder regions 620 and 622 are also present. Shoulder regions are formed, in part, by creation of the channels 604. The shoulder regions 618, 620, and 622 may also be created, in part, by milling or otherwise removing portions of the lower mold component 510 to form the corner regions, such as corner 624. However, in other cases the lower mold component may define a more smoothly varying shoulder region between the central area 608 and the inside diameter of the lower mold component 510, such as illustrated by dashed line 626. The specification now turns to the first disk member.

Figure 7:
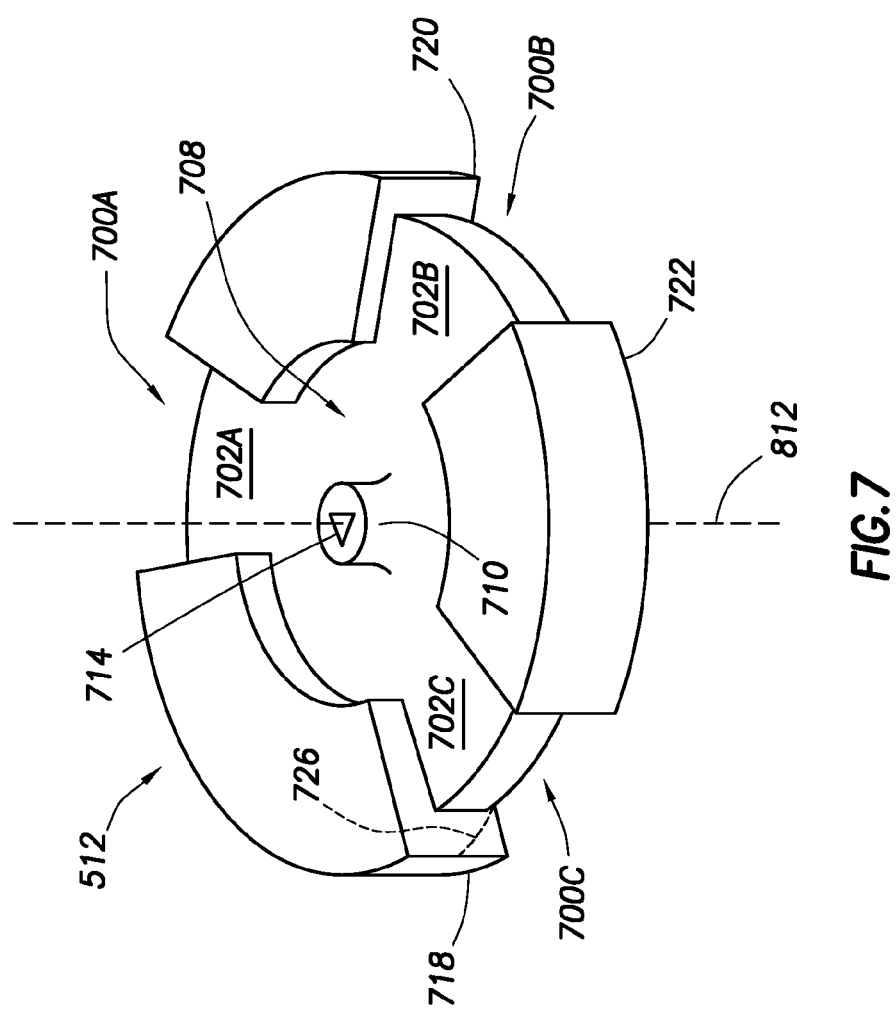
FIG. 7 shows a perspective view of an upper side of a first disk member in accordance with at least some embodiments.

FIG. 7 shows a perspective view of an upper portion of the disk member 512. In particular, disk member 512 is configured to telescope into and abut a portion of the mold surface 602 defined by the lower mold component 510. In the view of FIG. 7, the disk member 512 defines three channels 700A, 700B, and 700C on a lower surface of the disk member 512 (however, only channels 700B and 700C are visible in view of FIG. 7). When the disk member 512 is in the abutting configuration with the lower mold component 510, the channels 700 are aligned with the channels 604 of the lower mold component 510, and the channels define respective passageways from the central area 608 to the inside diameter of the lower mold component 510. There are additional features defined on the upper portion of the disk member 512, but a discussion of those additional features is presented after discussion of the features that abut or interact with the lower mold component 510.

Figure 8:
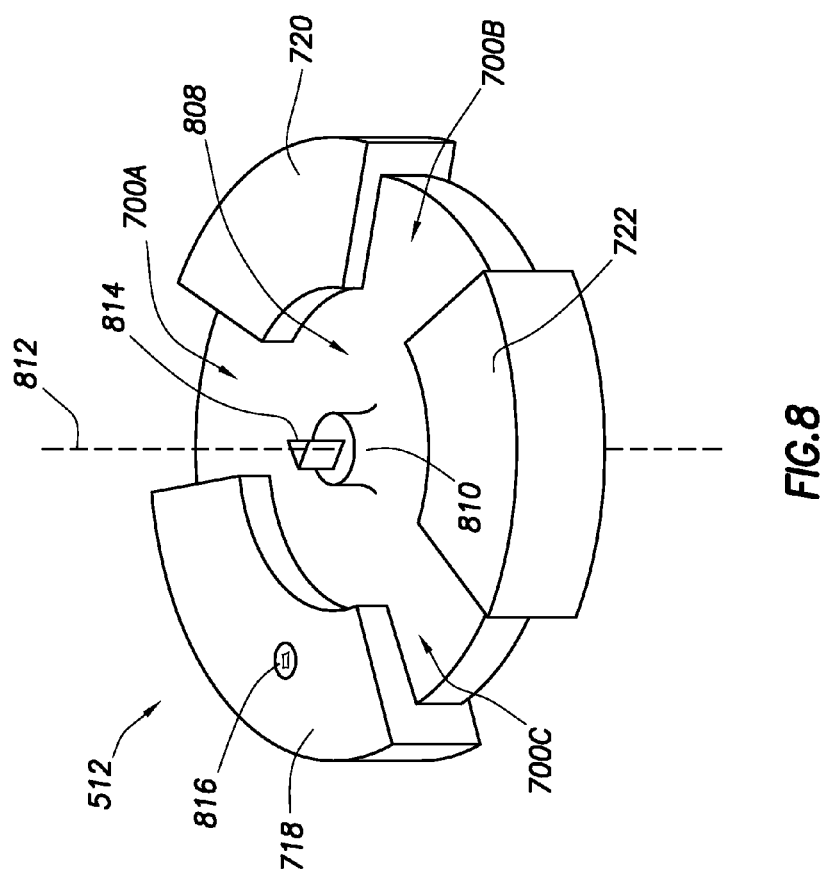
FIG. 8 shows a perspective view of a lower side of a first disk member in accordance with at least some embodiments.

FIG. 8 shows a perspective view of a lower portion of the disk member 512. In the view of FIG. 8, all three channels 700A, 700B, and 700C are visible. Moreover, the disk member 512 defines a central area 808 that corresponds to the central area 608 of the lower mold component 510 (i.e., the central area 808 and central area 608 have the same inside diameter). Also defined with the central area 800 is a protrusion or butte 810, which butte 810 may be centered along the longitudinal central axis 812, and further which butte 810 defines an alignment feature 814, illustrative shown as a triangular feature. Also visible in the view of FIG. 8 is an alternate alignment feature in the form a dimple feature 816, illustratively shown as a protruding out of the disk member 512.

Referring simultaneously to FIGS. 7 and 8, when the disk member 512 is in the abutting configuration with the lower mold component 510 (not shown in FIG. 7 or 8), the central axis 812 is coaxial with the central axis 612 of the lower mold component 510. Further, central area 808 of the first disk member 512 aligns with the central area 608 in the lower mold component. The central areas thus define a negative image of the flange member 114. Moreover, when the disk member 512 is in the abutting configuration with the lower mold component 510, the channels 700 are aligned with the channels 604 of the lower mold component 510, and the channels define respective passageways from the central area 800/608 to the inside diameter of the lower mold component 510. Stated otherwise, the channels define negative images of the stanchions 120. Further still, in the abutting configuration, the example alignment feature 814 of the disk member 512 telescopes into the alignment feature 614 defined in the butte 610 of the lower mold component 510, thus ensuring proper rotational alignment between the disk member 512 and the lower mold component 510. Moreover, in the abutting configuration of the disk member 512 with the lower mold component 510 the buttes 610/810 align and abut to define the negative image of the initial passageway 116. During the injection molding process the polymeric material in liquid form is forced into the channels and central area. After curing of the polymeric material, the polymeric sleeve may be removed from the lower mold component 510, the disk member 512 removed from beneath the flange member 114, and thus the flange member 114 and stanchion portions 120 of the polymeric sleeve 102 are formed.

Referring again to FIG. 7, a few additional features are discussed as a precursor to discussion of the second disk member 516. In particular, the disk member 512 defines a central area 708 on the upper portion. Also defined within the central area 708 is a protrusion or butte 710, which butte 710 may be centered along the longitudinal central axis 812, and further which butte 710 defines an alignment feature 714, illustrative shown as a triangular feature. A corresponding feature of the second disk member (discussed more below) has a shape that telescopes into the example alignment feature, thus ensuring proper rotational alignment. The location of the "male" alignment feature and the "female" alignment feature associated with the buttes may be equivalently reversed. Moreover, other alignment features may be used, such as dimple features as shown with respect to the lower mold component 510 and underside of the first disk member 512, but the various dimple features are not shown on the upper surface of the first disk member 512 (i.e., the view of FIG. 7) so as not to further complicate the drawings. The upper portion of the disk member 512 in FIG. 7 further shows a channels 702A, 702B, and 702C, wherein the channels extend from the central area 708 radially outward. In the example shown, the channels 702 align with the channels 700, but such alignment is not strictly required.

Finally, the example lower disk member 512 of FIG. 7 defines a series of lower shoulder regions 718, 720 and 722, which shoulder regions abut respective shoulder regions 618, 620, and 622 of the lower mold component 510 when the disk member 512 is stacked into an abutting relationship with the lower mold component 510. However, in other cases the lower mold component may define a more smoothly varying shoulder region, and thus the shoulder regions may be more smoothly varying (as shown by dashed line 726). The specification now turns to the second disk member.

Figure 9:
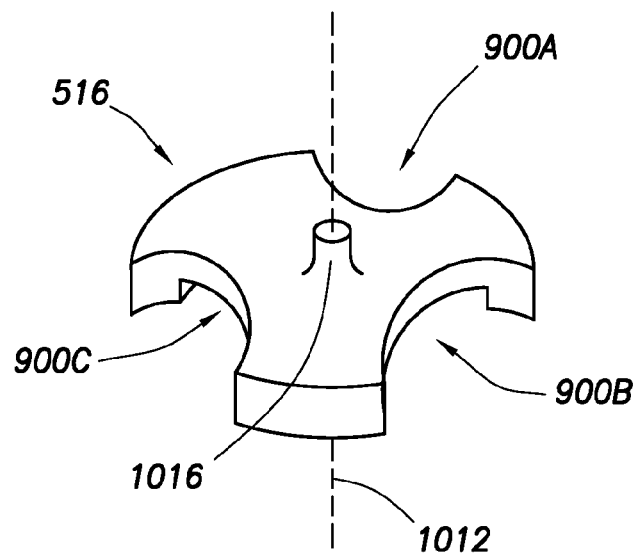
FIG. 9 shows a perspective view of an upper side of a second disk member in accordance with at least some embodiments.

FIG. 9 shows a perspective view of an upper portion of the second disk member 516. In particular, disk member 516 is configured to stack into the lower mold component and abut a portion of the first disk member 512. In the view of FIG. 9, the second disk member 516 defines three channels 900A, 900B, and 900C on the underside (however, only channels 900B and 900C are visible in view of FIG. 9). When the second disk member 516 is in the abutting configuration with the first disk member 512, the channels 900 align with the channels 702 on the upper surface of the first disk member 512, and the channels define respective passageways from the central area 708 radially toward the inside diameter of the lower mold component 510. There are additional features defined on the upper portion of the disk member 516, but a discussion of those additional features is presented after discussion of the features that abut or interact with the first disk member 512.

Figure 10:
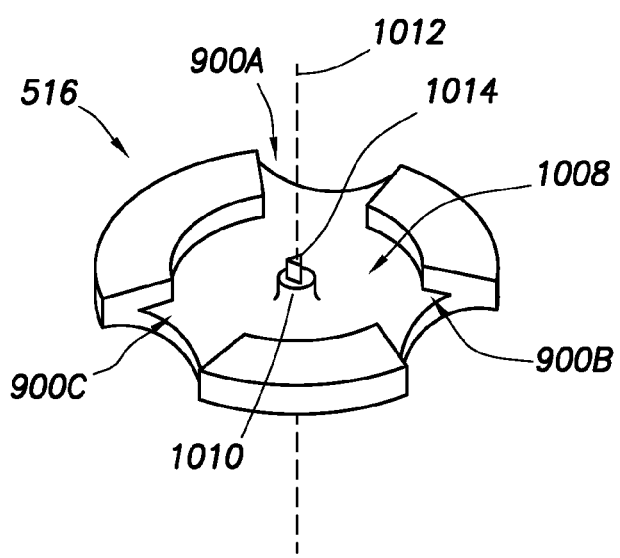
FIG. 10 shows a perspective view of a lower side of the second disk member in accordance with at least some embodiments.

FIG. 10 shows a perspective view of a bottom side of the disk member 516. In the view of FIG. 10, all three channels 900A, 900B, and 900C are visible. Moreover, the disk member 516 defines a central area 1008 that corresponds to the central area 708 of the first disk member 512 (i.e., the central area 1008 and central area 708 have the same inside diameter). Also defined with the central area 1008 is a protrusion or butte 1010, which butte 1010 may be centered along the longitudinal central axis 1012, and further which butte 1010 defines an alignment feature 1014, illustrative shown as a triangular feature. Other alignment features (such as the dimple features) may be used to rotationally align the second disk 516 and the first disk 512. However, those dimple features are not shown in-in FIGS. 9 and 10 so as not to further complicate the figures.

Referring simultaneously to FIGS. 9 and 10, when the second disk member 516 is in the abutting configuration with the first disk member 512, the central axis 1012 is coaxial with the central axis 812 of the first disk member 512. Further, central area 1008 of the second disk member 516 aligns with the central area 708 in the second disk member 512. The central areas thus define a negative image of the flange member 314. Moreover, when the disk member 516 is in the abutting configuration with the first disk member 512, the channels 900 are aligned with the channels 702 of the second disk member, and the channels define respective passageways from the central area 1008/708 toward the inside diameter of the lower mold component 510. Stated otherwise, the channels define negative image of the stanchions 320. Further still, in the abutting configuration the example alignment feature 1014 of the second disk member 516 telescopes into the alignment feature 714 defined in the butte 710 of the first disk member 512, thus ensuring proper rotational alignment between the first disk member 516 and the second disk member 512. The location of the "male" alignment feature and the "female" alignment feature associated with the buttes may be equivalently reversed. Moreover, in the abutting configuration of the second disk member 516 with the first disk member 512 the buttes 1010/710 align and abut to define the negative image of the second initial passageway 316. During the injection molding process the polymeric material in liquid form is forced into the channels and central area. After curing of the polymeric material, the polymeric sleeve may be removed from the lower mold assembly 510, the disk member 512 removed from beneath the flange member 114, the disk member 516 removed from beneath the flange member 314, and thus the flange members 114, 314 and stanchion portions 120, 320 of the polymeric sleeve 102 are formed.

Referring again to FIG. 9, a few additional features are discussed. The upper portion of the second disk member 516 defines a protrusion or butte 1016, which butte 1016 may be centered along the longitudinal central axis 812. During stacking of the various components into the lower mold component 510, once the second disk member 516 is in place, the rod member 514 may couple to the butte 1016. Thus, the butte 1016 forms the negative image of the main aperture 112 into the elongate body 202.

Figure 11:
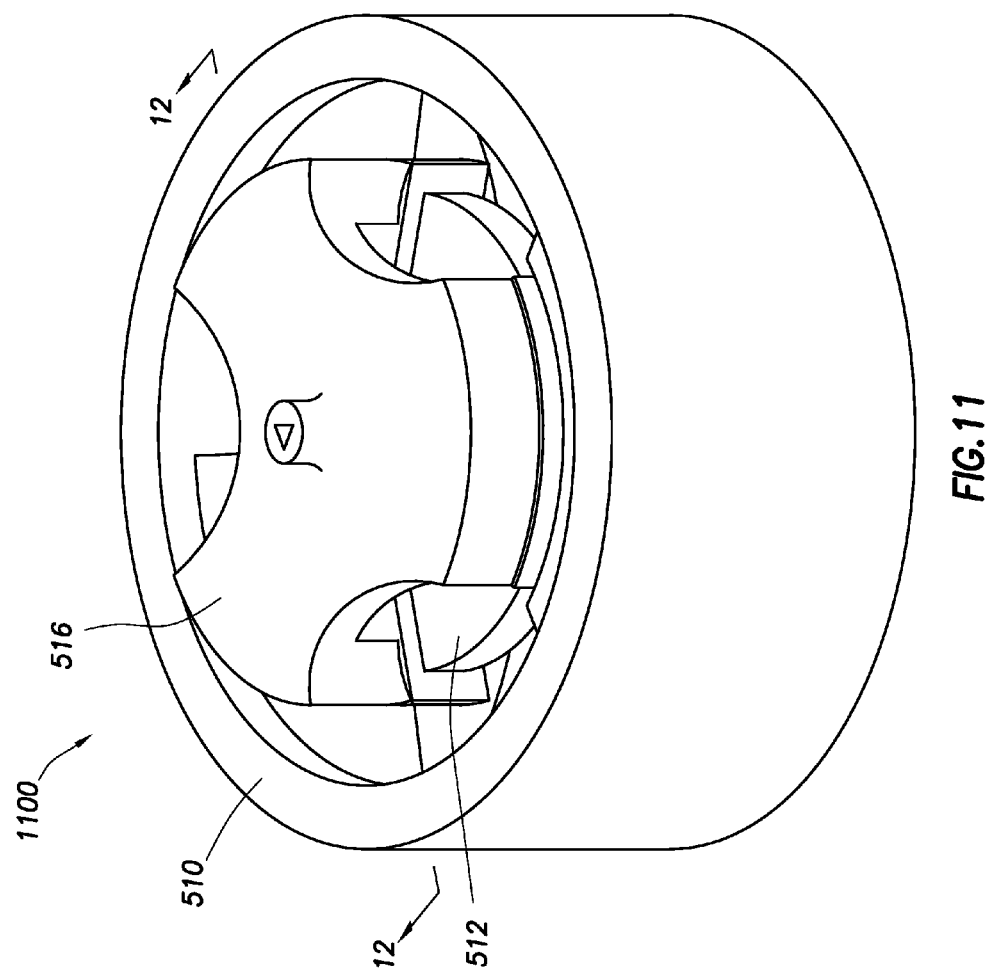
FIG. 11 shows a perspective view of a mold system in accordance with at least some embodiments.

FIG. 11 shows a perspective view of the various components that form the insertion end of the polymeric sleeve 102 stacked together in an abutting relationship (i.e., the mold system 1100). In particular, the lower mold component 510 is shown. Stacked within the lower mold component 510 is the first disk member 512. Stacked on top of the first disk member 512 is the second disk member 516. For the example system, notice how all the various channels align. As discussed above, the channels in the mold system form the stanchions that support the various flange members, and the central areas (none of which are visible in FIG. 11) form the flange members.

Figure 12:
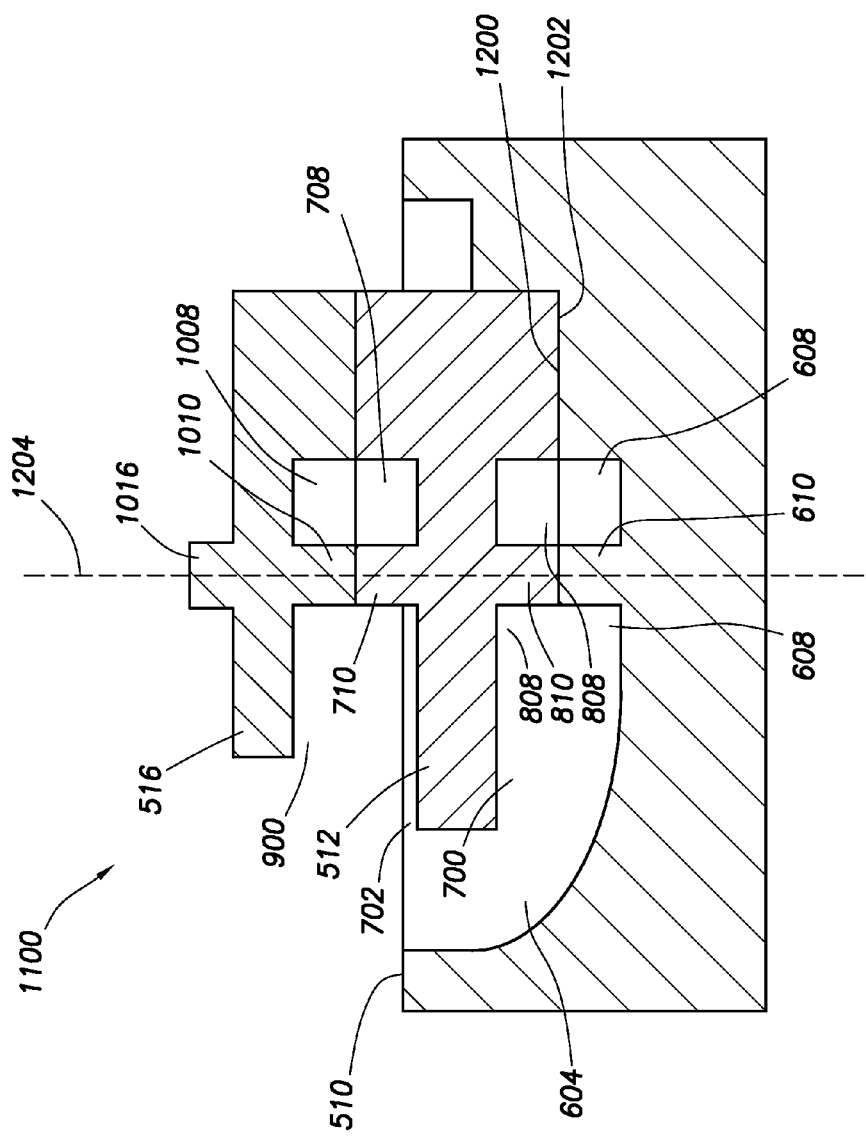
FIG. 12 shows a cross-sectional elevation view of a mold assembly in accordance with at least some embodiments.

FIG. 12 shows a cross-sectional, elevation view of the mold system 1100 of FIG. 11 taken substantially along lines 12-12 of FIG. 11. In particular, shown in FIG. 12 is the lower mold component 510, including the central area 608, butte 610, and channel 604. Further, the first disk member 512 is shown in a stacked and abutting relationship with the lower mold component 510. For example, the butte 810 is shown abutting the butte 610, and shoulder region 1200 of the first disk member 512 (which shoulder area 1200 could be any of the shoulder regions 718, 720, and 722) is shown abutting shoulder area 1202 of the lower mold component 510 (which shoulder area 1202 could be any of the should areas 618, 620, 622). Moreover, central area 808 is shown, along with channel 700.

FIG. 12 further shows the second disk member 516 in a stacked and abutting relationship with the first disk member 516. For example, the butte 710 is shown abutting the butte 1010. Moreover, central areas 708 and 1008 are shown, along with channels 702 and 900. Finally, butte 1016 is shown. In the stacked configuration, the central axis of each individual components are coaxial, as shown by dashed line 1204.

Figure 13:
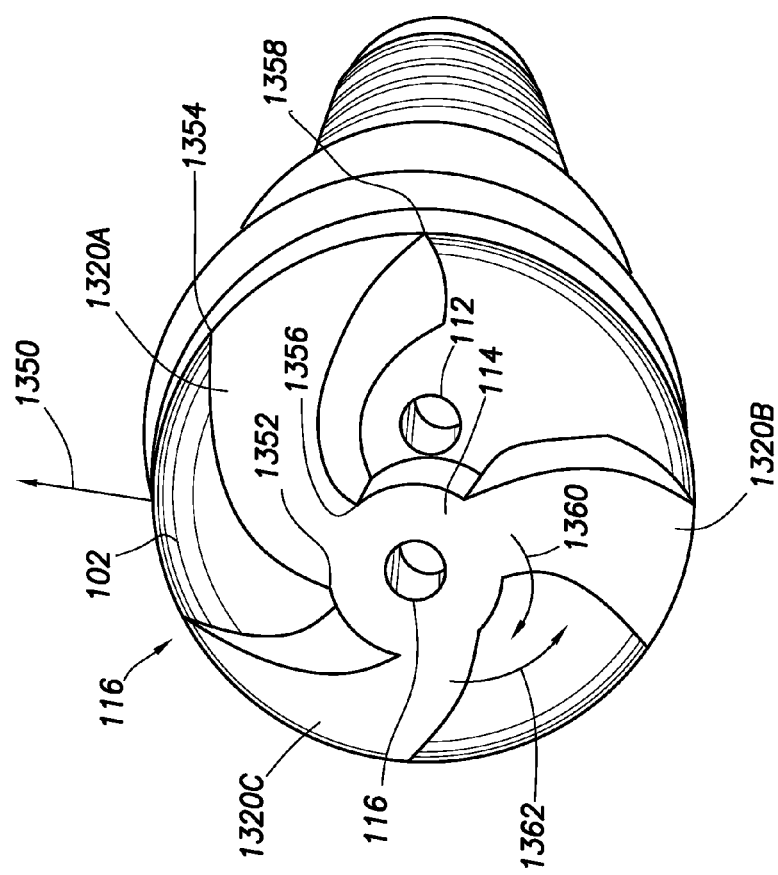
FIG. 13 shows a perspective view of a system in accordance with at least some embodiments.

The insertion end 116 shown in FIG. 1 is merely an example. Now understanding how to create such an insertion end using an injection molding process based on reading this specification, one of ordinary skill in the art could see that many variations in the outward appearance of the insertion end 116 could be made without departing from the scope and spirit of the various embodiments. For example, FIG. 13 shows a perspective view of an example insertion end 116 in accordance with other systems. In the example system, the stanchion portions 1320 extend from the outer perimeter of the insertion end 116 to the flange member 114, but in this case the stanchion portions are curved or arched such that the cardinal orientation of the location where each stanchion portion 1320 intersects the outer perimeter is different than the cardinal orientation where the stanchion portion 1320 intersects the flange member 114. For example, if the arrow 1350 represents a zero degree cardinal direction in relation to the insertion end 116, the intersection location 1352 where stanchion portion 1320A meets the flange member 114 may be considered to be at the zero degree cardinal direction, but the corresponding location 1354 where the stanchion portion 1320A meets the outer perimeter may be shifted between 10 and 45 degrees (in this case, clockwise when viewing the insertion end 116 from the view of FIG. 13). The corresponding locations 1356 and 1358 may likewise be shifted between 10 and 45 degrees. Some or all the stanchions portions may have the cardinal direction shift.

The "swirl" pattern of the insertion end 116 in FIG. 13 may result in an operational characteristic not present in other cases (such as FIG. 1). In particular, as mentioned above, during insertion of the penis into the aperture 116 the flange member tends to collapse toward the main aperture 112. However, during withdrawal of the penis, the flange member 114 tends to be not only pulled away from the main aperture 112, but also pulled further away from the main aperture than the resting position (shown in FIG. 13). The shifting in cardinal direction of the intersection locations of the stanchions portions between the flange member 114 and outer perimeter may result in a rotational aspect during withdrawal of the penis. In particular, during withdrawal, as the stanchion portions 1320 stretch, the offset in cardinal orientation may result in a rotational movement of the flange portion 114, the rotational movement illustrated by arrow 1360. The rotational movement is caused by the tangential component of the tension placed on the flange member 114 during periods when the flange member is stretched away from the (un-stretched) rest orientation (i.e., during withdrawal of the penis). As the tension in the stanchion portions is released, the loss of the tangential component of the tension may enable the flange member 114 to rotate back to its rest configuration (the rotation shown by arrow 1362).

Although several parameters of the example systems affect the stimulation provided by the polymeric sleeve 102 (e.g., elasticity of the polymeric material, diameter of the apertures defining the passageways, etc.), the various embodiments comprising at least one flange member are believed to better simulate the physical feel of fellatio.

FIG. 14 shows, in block diagram form, a method in accordance with at least some embodiments. In particular, the method starts (block 1400) and comprises: placing a lower mold component, the lower mold component structurally defines a negative image of an insertion end of a polymeric sleeve (block 1402); stacking into mating relationship a first disk member, the first disk member structural defines a negative image of an anterior volume vented to atmosphere on the insertion end of the polymeric sleeve (block 1404); stacking a second disk member into mating relationship with the first disk member, the second disk member structural defines a negative image of a posterior volume vented to atmospheric pressure (block 1406); coupling a rod member to the disk members, an exterior surface of the rod member defines a negative image of a main passageway through the polymeric sleeve (block 1408); closing an outer mold assembly around the lower mold component, the disk member, and the rod member, an interior surface of the outer mold assembly structurally defines a negative image of an outer surface of the polymeric sleeve (block 1410); and injecting a polymeric compound in a liquid state into the outer mold assembly (block 1412). Thereafter, the method ends (block 1414), likely to be repeated again with the same mold assembly.

References to "one embodiment," "an embodiment," "some embodiments," "example embodiments," or the like indicate that a particular element or characteristic is included in at least one embodiment of the invention. Although the phrases may appear in various places, the phrases do not necessarily refer to the same embodiment.

The above discussion is meant to be illustrative of the principles and various embodiments of the present invention. Numerous variations and modifications will become apparent to those skilled in the art once the above disclosure is fully appreciated. For example, an outer cover is not strictly required to use the polymeric sleeve. It is intended that the following claims be interpreted to embrace all such variations and modifications.

What is claimed is:

1. A system comprising:
    a polymeric sleeve comprising:
        an elongate body that defines a first end, a second end opposite the first end, and a longitudinal central axis;
        a main passageway through the elongate body parallel to the central axis, the main passageway extends from the first end to the second end, and the main passageway defines a first aperture on the first end and a second aperture on the second end;
        a first member suspended over the first aperture on the first end, the first member defines a first initial passageway parallel to the main passageway, and the first member and first end define an interior volume; and
        a first vent opening defined in part by the first member, the first vent opening distinct from the passageways, and the first vent opening fluidly couples the interior volume to atmosphere pressure.

2. The system of claim 1 wherein the main passageway is coaxial with the longitudinal central axis of the elongate body.

3. The system of claim 1 wherein the first initial passageway is coaxial with the main passageway.

4. The system of claim 1 wherein the polymeric sleeve further comprises:
    a second member suspended between the first member and the first aperture in the interior volume, the second member defining a second initial passageway parallel to the main passageway, and the second member bifurcates the interior volume into an anterior volume and a posterior volume; and
    a second vent opening defined in part by the second member, the second vent opening distinct from the passageways, and the second vent opening fluidly couples the posterior volume to atmospheric pressure.

5. The system of claim 4 further comprising the second vent opening fluidly couples the posterior volume to the anterior volume.

6. The system of claim 4 further comprising at least one selected from the group consisting of: the second initial passageway is coaxial with the first initial passageway; the second initial passageway is coaxial with the main passageway; and the passageways are coaxial.

7. The system of claim 1 further comprising an outer cover of rigid material that defines an interior volume, wherein the elongate body is at least partially disposed within the outer cover.

8. A system comprising:
    an outer cover of rigid material, the outer cover defines an interior volume;
    a polymeric sleeve at least partially disposed in the interior volume of the outer cover, the polymeric sleeve comprising:

an elongate body that defines a first end, a second end opposite the first end, and a longitudinal central axis;

a main passageway through the elongate body parallel to the central axis, the main passageway extends from the first end to the second end, and the main passageway defines a first aperture on the first end and a second aperture on the second end;

a first member suspended over the first aperture on the first end, the first member defines a first initial passageway parallel to the main passageway, and the first member and first end define an interior volume; and a first vent opening defined in part by the first member, the first vent opening distinct from the passageways, and the first vent opening fluidly couples the interior volume to atmosphere pressure;

wherein the first member resides outside the interior volume of the outer cover.

9. The system of claim 8 wherein the main passageway is coaxial with the longitudinal central axis of the elongate body.

10. The system of claim 8 wherein the first initial passageway is coaxial with the main passageway.

11. The system of claim 8 wherein the polymeric sleeve further comprises:

a second member suspended between the first member and the first aperture in the interior volume, the second member defining a second initial passageway parallel to the main passageway, and the second member bifurcates the interior volume into an anterior volume and a posterior volume; and a second vent opening defined in part by the second member, the second vent opening distinct from the passageways, and the second vent opening fluidly couples the posterior volume to atmospheric pressure.

12. The system of claim 11 further comprising the second vent opening fluidly couples the posterior volume to the anterior volume.

13. The system of claim 11 further comprising at least one selected from the group consisting of: the second initial passageway is coaxial with the first initial passageway; the second initial passageway is coaxial with the main passageway; and the passageways are coaxial.

14. The system of claim 8 wherein the second end of the elongate body resides within the interior volume of the outer cover.

15. The system of claim 8 further comprising:

a first cap member configured to telescope over the first member and removably couple the outer cover; and a second cap member configured to removably couple to the outer cover opposite the first cap member.

* * * * *

UNITED STATES PATENT AND TRADEMARK OFFICE
CERTIFICATE OF CORRECTION

| | | |
|---|---|---|
| PATENT NO. | : 9,039,600 B2 | Page 1 of 1 |
| APPLICATION NO. | : 13/796223 | |
| DATED | : May 26, 2015 | |
| INVENTOR(S) | : Steven A. Shubin, Sr. et al. | |

It is certified that error appears in the above-identified patent and that said Letters Patent is hereby corrected as shown below:

In the specification,

Column 11, line 46, "in-in" should read --in--.

Signed and Sealed this
Sixth Day of October, 2015

Michelle K. Lee
*Director of the United States Patent and Trademark Office*